United States Patent [19]

Dorsett

[11] Patent Number: 4,804,624

[45] Date of Patent: * Feb. 14, 1989

[54] PASSIVE AGGLUTINATION ASSAY FOR PSEUDORABIES ANTIBODY

[75] Inventor: Preston H. Dorsett, Memphis, Tenn.

[73] Assignee: The University of Tennessee Research Corporation, Knoxville, Tenn.

[ * ] Notice: The portion of the term of this patent subsequent to Sep. 22, 2004 has been disclaimed.

[21] Appl. No.: 663,853

[22] Filed: Oct. 22, 1984

Related U.S. Application Data

[63] Continuation-in-part of Ser. No. 380,537, May 21, 1982, Pat. No. 4,590,156.

[51] Int. Cl.$^4$ ................. G01N 33/569; G01N 33/546; C12Q 1/70
[52] U.S. Cl. ......................................... 435/5; 435/259; 435/810; 435/7; 436/533; 436/534; 436/543; 436/825; 427/2
[58] Field of Search ....................... 435/5, 7, 235, 810, 435/259; 436/533, 534, 543, 825; 427/2

[56] References Cited

U.S. PATENT DOCUMENTS

| | | | |
|---|---|---|---|
| 4,264,766 | 4/1981 | Fischer | 536/51 |
| 4,362,531 | 12/1982 | de Steenwinkel et al. | 436/534 X |
| 4,419,453 | 12/1983 | Dorman et al. | 436/534 |
| 4,562,147 | 12/1985 | Joo | 435/5 |
| 4,578,269 | 3/1986 | Morein | 424/88 |
| 4,588,680 | 5/1986 | Bucher et al. | 435/5 |
| 4,590,156 | 5/1986 | Dorsett | 435/5 |
| 4,695,537 | 9/1987 | Dorsett | 435/5 |

FOREIGN PATENT DOCUMENTS

| | | |
|---|---|---|
| 0054249 | 6/1982 | European Pat. Off. . |
| 0133200 | 2/1985 | European Pat. Off. . |

OTHER PUBLICATIONS

Wilson et al., Proceedings of the 3rd Internat'l Symposium—World Assoc. of Veterinary Lab. Diagnosticians, pp. 215–219 (1983).
Hill et al., Proceedings of the 3rd Internat'l Symposium—World Assoc. of Veterinary Lab. Diagnosticians, pp. 235–240 (1983).
Ladin et al., Virology 116:544–561 (1982), "Pathway of Assembly of Herpesvirus Capsids: An Analysis Using DNA Temperature-Sensitive Mutants of Pseudorabies Virus".
Chemical Abstracts: vol. 90, No. 1, p. 411, 1979.
Chemical Abstracts: vol. 97, No. 3, p. 19, 1982.

Primary Examiner—Esther M. Kepplinger
Attorney, Agent, or Firm—Arnold, White & Durkee

[57] ABSTRACT

A latex agglutination assay to detect antibodies against pseudorabies virus is provided. The test assays swine serum or plasma for the presence of pseudorabies virus antibody which is indicative of an acute or previous infection or vaccination. The latex reagent is a suspension of latex particles, 0.9 microns in diameter, that have adsorbed thereon antigens from disrupted and solubilized pseudorabies virus. When this material is mixed by rotation with serum containing pseudorabies antibodies, the latex will agglutinate forming visible clumps. In the absence of antibody, the latex suspension will remain smooth and evenly dispersed.

19 Claims, No Drawings

PASSIVE AGGLUTINATION ASSAY FOR PSEUDORABIES ANTIBODY

Benefit for this continuation-in-part application is claimed under 35 U.S.C.§ 120 of the prior co-pending application Ser. No. 380,537 filed May 21, 1982, issued as U.S. Pat. No. 4,590.156 on May 20, 1986.

BACKGROUND OF THE INVENTION

The present invention relates generally to materials and methods useful for the detection of antibodies; in particular, the invention relates to immunoreagents and immunodiagnostic tests for the detection of pseudorabies antibody in serum samples.

Pseudorabies is an infectious bulbar paralysis also known as mad itch or Aujeszky's disease. Its causitive agent is pseudorabies virus which is a herpes virus suis belonging to the family of Herpesviridae. Pseudorabies is mainly a disease of swine and cattle.

Swine, which is probably the natural host reservoir, infected with pseudorabies often show no symptoms. Infrequently, however, adult swine develop fever and neurological symptoms. Although many infected swine show no symptoms, the virus infection becomes latent and remains for the life of the animal.

In cattle, pseudorabies is a rapidly fatal non-suppurative encephalomyelitis characterized by intense pruritus and self mutilation. Affected cattle generally die within three days of the onset of clinical signs.

Since swine are generally regarded as the natural host and usual reservoir of pseudorabies virus, it is imperative to diagnose psueudorabies in swine before the swine intermingle with cattle. Bovine pseudorabies is prevented only by keeping swine separate from cattle. Although vaccines have been developed which are effective for swine, there is no effective vaccine for cattle.

A serological test for the detection of antibodies to pseudorabies virus is a valuable aid in identifying persistently infected pigs. However, current methods for antibody detection of pseudorabies are time consuming and often not sensitive enough to detect very low levels of antibody. In testing swine, the microtiter neutralization (SVN) test is the commonly employed method (Hill et al, *Proceedings of the American Association of Veterinary Laboratory Diagnosis*, 20:375-390 (1977)). Significant disadvantage is incurred with the SVN test. The SVN test involves a three to four hour set-up time plus a forty-eight hour incubation time. Another serious drawback of the SVN test is that it involves a biohazard risk associated with the use of infectious virus.

Accordingly, there remains a need for an improved immunodiagnostic test for pseudorabies virus antibody. The present invention provides a safe, reliable, efficient, reproducible and sensitive assay for the detection of serum pseudorabies virus antibody.

SUMMARY OF THE INVENTION

The present invention provides a latex composition and methods for its use to detect the presence of pseudorabies virus antibody in a biological sample.

The latex composition of this invention is composed of pseudorabies virus antigens physically adsorbed onto or covalently bound to discrete latex particles. The pseudorabies virus antigens are the products of disrupted and solubilized pseudorabies virus. The disrupted pseudorabies virus products provide a variety of pseudorabies virus antigens which are selectively immunoreactive with pseudorabies virus antibody. In particular, the use of the disrupted virus avoids the biohazard associated with infectious virus. Moreover, adsorption of the disrupted, solubilized virus antigens to the latex particles results in a smooth latex dispersion in contrast to the aggregated, clumped latex particles which result after adsorption of whole intact virus.

In the methods of this invention, the latex composition is employed in a direct agglutination assay to detect the presence of pseudorabies virus antibody in a biological sample. The test involves admixing a biological sample, such as serum, with the latex composition. The admixture is incubated under conditions favorable for immunoreaction. Thereafter the admixture is examined macroscopically for agglutination or clumping of the latex particles. Agglutination is indicative of the presence of pseudorabies virus antibody in the biological sample.

DETAILED DESCRIPTION OF THE PREFERRED EMBODIMENT

The following discussion is in terms of the preferred embodiments of this invention, which represent the best mode known to the Applicants at the time of this application.

In accordance with this invention a latex composition is provided which is of particular value in a direct agglutination assay for pseudorabies virus antibody. The latex composition of this invention consists essentially of disrupted and solubilized pseudorabies virus products supported on a latex carrier particle.

LATEX

As used within the context of this invention, latex carrier particles include latex polymers which are water insoluble, have a particle size in the range of about 0.05 microns to about 2.0 microns, have a specific gravity near that of water so that they can remain in aqueous suspension, and are inert with respect to immunological reactions. Further, the latex particles must have sufficient repulsive forces after adsorption of the pseudorabies virus antigen so as to prevent their aggregation in the absense of an immunological reaction.

Typical suitable latex carrier particles are those supplied commercially as an aqueous latex suspension, usually in concentrations of about 20 to about 60% solids. Many types of latex are suitable for use in this invention so long as they meet the criteria listed above.

Typical sutable latex carrier polymers are carboxylated polystyrenes, acrylic acid polymers, methacrylic acid polymers, acrylonitrile butadiene styrenes, polyvinyl acetate acrylates, polyvinyl pyridines, vinyl choloride-acrylates, and the like. Some commercially available latexes suitable for use in this invention are AMSCO Res 4150, AMSCO Res. 3011 (American Mineral Spirits Co.); Dow Latex 815; 816; 620; or 859 (The Dow Chemical Co.); Hycar 1512, Hycar 1877x8, Hycar 2600x 120 (Goodrich Chemical Co.); Gelva 900, Lytron 612, Lytron 624 (Monsanto); Rhoplex LC 403216, Amberlite Ultrafine (Rohn and Hass); and Bacto-latex 0.81 (Difco Laboratories).

PSEUDORABIES VIRUS ANTIGEN

Further in accordance with this invention partially purified pseudorabies virus antigens are provided for attachment, by adsorption or covalent binding, to the latex particles. The pseudorabies virus antigens are the product of disrupted and solubilized pseudorabies virus.

The pseudorabies whole virus is first produced in tissue culture by procedures known in the art. In particular, pseudorabies virus can be grown in swine testes cells, primary pig kidney cells, a PK-15 cell line, primary rabbit kidney cells, and a swine fibroblast cell line, MDBK.

After filtration and concentration of the pseudorabies virus-containing fluid obtained from cell culture, the pseudorabies virus is then purified. More particularly, after filtration and concentration, the virus is contacted with hydroxyl apatite slurry in an aqueous suspension having an ionic strength which is great enough to minimize or prevent adsorption of the virus by the gel, and which is low enough to allow some of the non-virus proteins to be adsorbed by the hydroxyl apatite gel. The ionic strength is maintained by the use of a phosphate buffer, with the phosphate ions being present at a molarity of about 0.001M. This ionic strength provides effective adsorption of non-virus proteins and nucleic acids, without significant adsorption of the virus. The phosphate molarity in most cases is between 0.001 to 0.005M.

In addition, the adsorption is conducted at a pH in the order of from 6 to 10, most generally in the order of from 8 to 9. The pH of the solution is maintained by the use of a suitable buffer. The adsorption may be conducted in the presence of EDTA at a concentration from 0.01M to 0.0001M. EDTA as well as other chelating agents increases adsorption of non-viral proteins and nucleic acids, and aids in minimizing the adsorption of viral proteins.

In proceeding with the purification, the high molecular weight proteins and nucleic acids are adsorbed by the gel to thereby separate the virus protein from the non-viral proteins havng similar molecular weights.

After such adsorption, the lower molecular weight proteins still remaining in the fluid may be separated by conventional procedures. Thus, for example, further separation may be accomplished by centrifugation through a barrier layer or cushion as known in the art. In particular, the virus protein is centrifuged through a suitable barrier layer such as sucrose, glycerol, cesium chloride, cesium sulfate and the like, with the lower molecular weight proteins remaining above the barrier, and the virus being centrifuged through the barrier, as a separate layer. The fluid containing the low molecular weight proteins and the barrier layer is then removed leaving a virus protein essentially free of non-virus proteins, nucleic acids, lipids, and the like. In general, the purified virus contains less than 1%, most generally less than 0.1% of non-virus lipids, nucleic acids and proteins.

Such purified virus may then be treated with a surfactant to disrupt the virus and effect solubilization to provide soluble viral antigens.

Pseudorabies virus antigen is prepared from intact pseudorabies virus by treating purified whole pseudorabies virus with a surfactant or detergent which disrupts the virus to provide the soluble pseudorabies virus antigen, without destroying its antigenic characteristics. The detergent is employed in an amount that is sufficient to disrupt and solubilize the whole virus without destroying antigenicity. In general the surfactant to virus weight ratio is from 0.2:1 to about 5:1, preferably from about 0.4:1 to 1:1.

The surfactant or detergent which is used for disrupting the whole pseudorabies virus may be any one of a wide variety of surfactants or detergents, including cationic, anionic and non-ionic surfactants Such surfactants are well known in the art, and as representative examples, there may be mentioned alkali metal salts of sulfates, soaps, sulfated or sulfonated oils, various amines, quaternary salts, condensation products with ethylene oxide, etc. Preferred detergents for such use are alkali (lithium or sodium) dodecyl sulfate, sulfobetain, deoxylcholate and laurolylsarcosine (Sarcosyl).

The treatment of the purified virus is effected at a temperature which does not denature the virus proteins, with such temperature generally not exeeding about 37° C., with a temperature from 20° to 37° C. being most convenient. Similarly, the pH is selected so as to maintain stability, with the pH being generally at 8.5, with the optimum pH generally being in the order of from 8.0 to about 9.0.

The treatment of the purified virus with the surfactant is for a period of time sufficient to disrupt the virus and effect solubilization thereof. In general, such disruption and solubilization can be accomplished in time periods in the order of from 5 to 120 minutes, however, in some cases longer or shorter times may be applicable.

LATEX SUPPORTED PSEUDORABIES VIRUS ANTIGEN COMPOSITION

After recovering the disrupted pseudorabies virus products they are attached by passive adsorption to the latex carrier particles. The antigen is adsorbed to the latex in an effective amount to facilitate the agglutination assay, but in an amount low enough to prevent bridging of the antibody on a single particle. In general, the weight ratio of soluble antigen to support is from about 1:30 to about 1:200; and 1:50 to 1:100 is the preferred range.

In addition to passive adsorption techniques, the disrupted pseudorabies virus products can be covalently bound to the latex carrier. In particular, U.S. Pat. Nos. 4,264,766, and 4,210,723, incorporated herein by reference, provide numerous latex particles having active groups which are capable of forming covalent linkages with immunologically active substances such as the disrupted pseudorabies virus antigen products of this invention.

In accordance with yet another embodiment of this invention, after the antigen is adsorbed onto the latex particles, the support, including the adsorbed antigen, is further coated with an immunologically inert protein, such as bovine serum albumin or ovalbumin, which does not react with the pseudorabies antigen or adversely affect the subsequent immunochemical reaction with the antibody.

The pseudorabies virus antigen sensitized particles prepared in accordance with this invention are suitable for use in a kit and assay for pseudorabies virus antibody by a direct agglutination procedure. Such a kit may include, in addition to the sensitized pseudorabies virus particles in a suitable container, a reactive serum control containing pseudorabies antibody, and a non-reactive serum control in suitable containers therefor. In accordance with a preferred embodiment, in addition to the reagents, there is provided a test slide on which the assay is effected. The test slide has a flat testing surface which include suitably marked areas (for example, a test circle) for placing one or more samples to be assayed, as well as suitably marked areas for each of the serum controls. The test slide and reagents may be included in a single kit package.

DIRECT AGGLUTINATION ASSAY

The antigen-antibody reaction is the basis for all immunological assays. Antibodies are produced by mammals in response to the presence of a foreign substance called an antigen, usually a protein. This normal body response to a foreign protein, including bacterial and viral agents, has led to the development of a number of techniques useful to diagnose mammalian infection or disease.

In vitro tests for detecting antibody in a biological sample are generally carried out by cottacting the antigen with a biological sample. If the suspected antibody is present, the resulting antigen-antibody reaction can be demonstrated by precipitation or agglutination of the antigen-antibody complex. This antigen-antibody reaction is usually very difficult to detect visually. By binding the test antigens to a particulate carrier, such as latex, the subsequent antigen-antibody agglutination reaction becomes readily visible. Agglutination is characterized by the macroscopic clumping of the latex particles from an otherwise smooth suspension.

In a direct latex agglutination test for the detection of pseudorabies antibody in a biological sample, such as swine serum, the biological sample is mixed with a suspension of the latex supported pseudorabies antigen. If pseudorabies antibody is present in the biological sample, it will react with the antigen to form a precipitate or aggregate of the latex particles. If no pseudorabies antibody is present, the latex suspension will keep its appearance as a smooth suspension.

To facilitate specific antibody-antigen reaction, swine serum can, prior to the assay, be adsorbed with kaolin, bentonite, apatite, talc, or charcoal to reduce its lipid content and nonspecific binding agents. Alternatively, the serum can be used at a 1:4 to 1:10 dilution which eliminates most nonspecific reactions.

EXAMPLE I

Production and Purification of Pseudorabies Virus

Sullivan strain pseudorabies virus was originally isolated from a natural infection of a pig in Camden, Ind. The virus was obtained from Dr. D. P. Gustafson, Purdue University. At Wisconsin State University, the virus had been passaged once in adult pig thyroid cell monolayers. Afterwards, it was plaqued purified three times in a continuous culture swine testes cells. Plaque purified virus in the fourth passage in swine testes cells were used for these experiments.

Confluent roller cultures (680cm$^2$) of swine testes cells were innoculated with approximately 0.01 PFU of pseudorabies virus per cell and maintained in a standard culture medium (Medium 199) containing 0.025M hepes buffer, pH 7.6, and 5% (vol/vol) of tryptose phosphate broth. The cells were incubated from 48–96 hours at 36±1° C. Harvested by freezing at −70° C., the cells were next thawed to disrupt residual cells. Afterward the thawed material was centrifuged differentially, first at 4000×g then at 16,000×g each for 15–20 min. The supernatant was concentrated in an Amicon hollow fiber dialyzer-concentrator to 1/6 the original volume. After clarification at 5,000×g, the concentrate was made to contain 0.001M EDTA, the pH was adjusted to 8.5 at 22° C. room temperature, and the concentrate was clarified at 16,000×g. Next 1/10 volume of hydroxylapatite suspension was added, and the slurry was incubated at 4° C. with mixing, for one hour. The hydroxylapatite was removed by centriguation at 16,000×g for 15 minutes, after which 30 ml of the concentrate was layered over 9 ml of 69% (wt/wt) glycerol in a Beckman SW28 tube. The virus was sedimented at 82,000×g for 16 hours at 4° C., and the resultant pellet was resuspended in NTE buffer: 0.01M Tris containing 0.12M NaCl and 0.001 MEDTA, pH 8.5. The purified virus was stored at −70° C.

EXAMPLE II

Solubilization of Purified Virus

The purified virus was dissolved in 1×NTE buffer and the protein content was determined by the O.D. 260/280 nm ratio. The virus was disrupted and solubilized by treatment with sodium dodecyl sulfate (SDS) at a concentration of 0.5 mg SDS per 1 mg of viral protein (w/w) for 30 minutes at 36°–37° C.

EXAMPLE III

Preparation of Sensitized Latex

Commercial suspensions of polystyrene latex (0.9 micron diameter particles) were washed four times with 50 volumes each of 0.01M carbonate pH 9.5 buffer and were resuspended in the carbonate buffer to provide 3% solids (vol/vol). The solubilized virus was added directly to the latex with mixing at a ratio of 0.4 mg of purified protein per ml of 3% latex. The suspension was mixed by tumbling for 16 hours at 4° C. The sensitized latex was diluted with an equal volumes of phosphate buffered saline. The latex was collected by centrifugation at 8000×g for 10 minutes and the pellet resuspended at 0.6% in 1% bovine serum albumin in phosphate buffered saline (BSA-PBS) containing 0.05% polyoxyethylene sorbitan monolaurate surface active agent (Tween 20) and 0.02% gentamicin. The sensitized latex was sonicated in 5 ml aliquots for 1 second at full power on a Bronson Model S75 Sonifier.

EXAMPLE IV

Latex Agglutination Test for Pseudorabies Virus Antibodies

Glass plates with 1.4 cm fused circles were employed. Serial 2-fold dilutions of serum were prepared in 1% BSAPBS containing Tween 20 and 50 ul of each dilution was placed in separate circles, and spread to cover the circle. After adding 15–20 ul (1 drop) of sensitized latex, the serum and latex suspension was mixed by hand or rotated at 100 rpm for 5–8 minutes. The slide was read macroscopically in the wet state. The presence of antibody against pseudorabies virus was evidenced by visible agglutination.

EXAMPLE V

A serum sample was mixed with an equal volume of 25% kaolin suspension. The mixture was allowed to stand at room temperature for 20 minutes. The kaolin was removed by centrifugation at 2000 rpm for 10 minutes. The resultant supernatant fluid was a 1:2 dilution of the serum. With a micropipettor, 25 ul of the supernatant fluid was placed into a fused circle on the glass slide. With the micropipettor, 25 ul of the sensitized latex reagent was then added to the same circle. The slide was rotated on a rotator at approximately 100 rpm for 8 minutes, while placed under a humidifier cover.

Immediately following rotation, the slide was read macroscopically in the wet state under a high intensity incandescent lamp. Positive tests were noted as a clumping of the latex. In negative tests, the latex remained in smooth suspension.

While the compositions and methods of this invention have been described in terms of preferred embodiments, it will be apparent to those of skill in the art that various changes may be made in the composition and methods disclosed without departing rom the scope of the invention, which is defined by the following claims.

What is claimed is:

1. A latex composition consisting essentially of discrete latex particles having attached thereon disrupted and solubilized pseudorabies virus providing antigens which are selectively immunoreactive with pseudorabies virus antibody.

2. The latex composition of claim 1 which is dispersed in a fluid suspension.

3. The latex composition of claim 1 which is dispersed in an aqueous suspension.

4. The latex composition of claim 1 wherein the weight ratio of disrupted and solubilized pseudorabies virus to latex particle is from about 1:30 to about 1:200.

5. The latex composition of claim 1 which further includes an immunologically inert protein adsorbed to the latex particles.

6. The latex composition of claim 5 wherein the inert protein adsorbed to the latex particles is bouvine serum albumin or ovalbumin.

7. The latex composition of claim 1 wherein the latex is polystyrene latex.

8. The latex composition of claim 1 wherein the latex particle ranges from about 0.05 to about 2.0 microns in diameter.

9. The latex composition of claim 1 wherein the latex particle is about 0.9 microns in diameter.

10. The latex composition of claim 1 wherein the disrupted and solubilized pseudorabies virus is passively adsorbed to the latex particles.

11. The latex composition of claim 1 wherein the disrupted and solubilized pseudorabies virus is covalently bound to the latex particles.

12. The latex composition of claim 1 wherein the disrupted and solubilized pseudorabies virus is produced from pseudorabies virus which has been disrupted and solubilized with a surfactant.

13. A method for detecting the presence of pseudorabies virus antibody in a biological sample comprising:
    providing a latex composition consisting essentially of disrupted and solubilized pseudorabies virus attached to latex particles, which latex particles are dispersed in a fluid suspension;
    admixing the biological sample with the latex composition to form a reaction mixture;
    incubating the reaction mixture for a time sufficient to allow an immunoreaction; and
    determining if agglutination occurs, whereby agglutination indicates the presence of pseudorabies virus antibody in the biological sample.

14. The method of claim 13 wherein the biological sample is serum or plasma.

15. The method of claim 13 wherein the biological sample is swine serum or plasma.

16. The method of claim 13 wherein before admixing with the latex composition the biological sample is pretreated with kaolin, talc, charocoal or apatite to remove nonspecific agglutinins.

17. The method of claim 13 wherein the biological sample is first diluted with an immunologically inert diluent prior to admixing with the latex composition.

18. The method of claim 13 wherein the latex composition consists essentially of disrupted and solubilized pseudorabies virus passively adsorbed to latex particles.

19. The method of claim 13, wherein the latex composition consists essentially of disrupted and solubilized pseudorabies virus covalently bound to latex particles.

* * * * *